United States Patent
Sigmund et al.

(10) Patent No.: US 7,541,509 B2
(45) Date of Patent: Jun. 2, 2009

(54) PHOTOCATALYTIC NANOCOMPOSITES AND APPLICATIONS THEREOF

(75) Inventors: Wolfgang M. Sigmund, Gainesville, FL (US); Sung-Hwan Lee, Seoul (KR); Benjamin Koopman, Gainesville, FL (US); Brij Moudgil, Gainesville, FL (US); Georgios Pyrgiotakis, Gainesville, FL (US); Vijay Krishna, Gainesville, FL (US)

(73) Assignee: University of Florida Research Foundation, Inc., Gainsville, FL (US)

( * ) Notice: Subject to any disclaimer, the term of this patent is extended or adjusted under 35 U.S.C. 154(b) by 558 days.

(21) Appl. No.: 11/216,303

(22) Filed: Aug. 31, 2005

(65) Prior Publication Data

US 2008/0045770 A1 Feb. 21, 2008

Related U.S. Application Data

(60) Provisional application No. 60/605,854, filed on Aug. 31, 2004.

(51) Int. Cl.
*A62D 3/00* (2007.01)
*A62D 3/17* (2007.01)
*A62D 3/10* (2007.01)
*B01J 37/00* (2006.01)

(52) U.S. Cl. .............. 588/299; 588/301; 588/306; 502/129

(58) Field of Classification Search ............... 502/299, 502/306
See application file for complete search history.

(56) References Cited

U.S. PATENT DOCUMENTS 5,449,443 A 9/1995 Jacoby et al.
6,306,343 B1 10/2001 Sugiyama
6,827,922 B2 12/2004 Sawabe et al.
7,253,014 B2 * 8/2007 Barron et al. ............... 438/34
2004/0067849 A1 4/2004 Tanaka et al.

FOREIGN PATENT DOCUMENTS

EP 1 462 169 A1 9/2004

OTHER PUBLICATIONS

Formation of Anatase TiO2 Nanoparticles on Carbon Nanotubes; Chem. Comm.; pp. 780-781; Feb. 21, 2003.*
Synthesis and Characterization of Carbon Nanotubes-TiO2 Nanocomposites; 42, pp. 1147-1151; Feb. 11, 2004.*

(Continued)

*Primary Examiner*—Melvin C Mayes
*Assistant Examiner*—Guinever S Gregorio
(74) *Attorney, Agent, or Firm*—Akerman Senterfitt

(57) ABSTRACT

A photocatalyst nanocomposite which can be used to destroying biological agents includes a carbon nanotube core, and a photocatalyst coating layer covalently or ionically bound to a surface of the nanotube core. The coating layer has a nanoscale thickness. A method of forming photocatalytic nanocomposites includes the steps of providing a plurality of dispersed carbon nanotubes, chemically oxidizing the nanotubes under conditions to produce surface functionalized nanotubes to provide C and O including groups thereon which form ionic or covalent bonds to metal oxides, and processing a metal oxide photocatalyst sol-gel precursor in the presence of the nanotubes, wherein a nanoscale metal oxide photocatalyst layer becomes covalently or ionically bound to the nanotubes.

20 Claims, 8 Drawing Sheets

OTHER PUBLICATIONS

Kulak et al. "Photoelectrochemical Behaviour of TiO2-Modified Carbon-Fibre Electrode Assembly", Proceedings of the 10th Workshop on Quantum Solar Energy Conversion, Mar. 8-14, 1998, Bad Hofgastein, Austria, 3 pages.

Kim et al. "Zinc sulfide nanocrystals on carbon nanotubes", 2003, Journal of Crystal Growth, 225:114-118.

Kim et al. "Zinc oxide nanowire on carbon nanotubes", 2002, Applied Physics Letters, 81(11):2085-2087.

Matsunaga et al. "Continuous-Sterliziation System That Uses Photosemiconductor Powders", 1988, Applied and Environmental Microbiology, 54(6):1330-1333.

Matsunaga et al. "Photoelectrochemical sterilization of microbial cells by semiconductor powders", 1985, FEMS Microbiology Letters, 29:211-214.

Jitianu et al. "Synthesis and characterization of carbon nanotubes-TiO2 nanocomposites", Carbon, (2004), vol. 42, pp. 1147-1151.

Hernadi et al. "Synthesis of MWNT-based composite materials with inorganic coating", Acta Materialia, (2003), vol. 51, pp. 1447-1452.

Huang et al. "Immobilization of rutile TiO2 on multiwalled carbon nanotubes", J. Mater. Chem., (2003), vol. 13, pp. 1517-1519.

Tamai et al. "Simple preparation of TiO2 particles dispersed activiated carbons and their photo-sterilization activity", Journal of Material Science, (2002), vol. 37, pp. 3175-3180.

Sun et al. "Development of a dispersion process for carbon nanotubes in ceramic matrix by heterocoagulation", Carbon, (2003), vol. 41, pp. 1063-1068.

Sun et al. "Single-walled carbon nanotubes coated with titania nanoparticles", Carbon, (2004), vol. 42, pp. 885-901.

* cited by examiner

PHOTOCATALYTIC NANOCOMPOSITES AND APPLICATIONS THEREOF

CROSS-REFERENCE TO RELATED APPLICATIONS

The present application claims the priority of U.S. provisional patent application No. 60/605,854 filed on Aug. 31, 2004 and entitled "Photocatalytic Nanocomposites and Applications Thereof".

STATEMENT REGARDING FEDERALLY SPONSORED RESEARCH OR DEVELOPMENT

The U.S. Government has certain rights to the invention based on National Science Foundation Grant No. EEC-94-02989.

FIELD OF THE INVENTION

This invention relates to photocatalyst coated nanotubes and applications thereof including use as a biocide.

BACKGROUND OF THE INVENTION

Certain bacteria can be harmful or even deadly to humans as well as animals. In September 2001, anthrax spores were mailed to several locations via the US Postal Service resulting in twenty-two confirmed or suspected cases of anthrax infection. Because the possibility of a terrorist attack using bio-weapons is especially difficult to predict, detect, or prevent in a conventional way, it is crucial to find a solution to nullify a microbial attack.

Currently, there is a lack of efficiency with the conventional method and further developments are necessary to achieve higher biocidal efficiency. Moreover, because of the widespread use of antibiotics and the emergence of more resistant and virulent strains of microorganisms, and furthermore bacterial spores have no metabolism and can withstand a wide range of environmental assaults including heat and UV, there is an immediate need to develop alternative sterilization technologies such as photoelectrochemical sterilization using highly efficient photocatalysts.

Wide band-gap semiconductors can act as sensitizers for light-induced redox processes due to their electronic structure, which is characterized at room temperate by a filled valence band and an empty conduction band. Hydroxyl radicals (OH.) generated by the Titania photocatalyst are very potent oxidants and are nonselective in reactivity.

Titania ($TiO_2$) is currently the photocatalyst of choice for most applications, being the most efficient known photocatalyst. Irradiation of a semiconductor, such as $TiO_2$, with light having an energy equal to or greater than the semiconductor material's band gap energy results in the creation of electrons in the semiconductor's conduction band and holes in its valence band. The injection of these electrons and holes into a fluid region surrounding the semiconductor particles causes electrochemical modification of substances within this region. This technology has been used in photocatalytic processes such as the photo-Kolbe reaction in which acetic acid is decomposed to methane and carbon dioxide and the photosynthesis of amino acids from methane-ammonia-water mixtures.

When irradiated $TiO_2$ particles are in direct contact with or close to microbes, the microbial surface becomes the primary target of the initial oxidative attack. In 1985, Matsunaga and coworkers reported that microbial cells in water could be killed by contact with a $TiO_2$—Pt catalyst upon illumination with near-UV light for 60 to 120 min. Later, the same group of workers constructed a practical photochemical device in which $TiO_2$ particles were immobilized on an acetylcellulose membrane. The loss of membrane structure and membrane functions due to the photochemical oxidation was the root cause of cell death when photocatalytic $TiO_2$ particles are outside the cell. It was observed that the extent of killing depended on the structure of the cell wall and was inversely proportional to the thickness. The findings of Matsunaga et al. redirected the attention for sterilization and resulted in an attempt to use this technology for disinfecting drinking water and removing bioaerosols from indoor air environments.

A variety of devices for air purification using Titania for photocatalytic degradation of organic impurities and microbial contaminates have been disclosed. The primary metal oxide for these devices is $TiO_2$. Typically the challenge was to have the impurity or contaminate in contact with the titania surface for a sufficiently long period of time to effectively remove the desired contaminate and often elaborate systems were designed to increase the effective contact time. In all of these cases, an improvement in the photocatalyst efficiency by increasing the efficiency of the $TiO_2$ would greatly enhance the effectiveness of these devices. Moreover, the ability to use photocatalysts for air purification using visible light or sunlight, as opposed to conventionally used UV light, is highly desirable.

SUMMARY OF THE INVENTION

The invention is directed to a photocatalyst nanocomposite wherein a surface of a carbon nanotube which preferably provides metallic electrical conductivity is covered with a nanoscale (<1 μm) thick photocatalyst coating layer. The photocatalyst coating is covalently or ionically bound to the nanotube core, and preferably has a thickness of 1 to 10 nm. The photocatalyst can be selected from $TiO_2$, ZnO, and $Fe_3O_4$ as well as non-metal oxide semiconductors, such as sulfides, selenides, nitrides and carbides. For example, useful non-metal oxide semiconductors include $MoS_2$, $WS_2$, $MoSe_2$, and $FeS_2$. The photocatalyst coating is preferably a continuous coating.

The surface of said nanotube preferably includes C and O comprising functionalities derived from oxidation of the surface. For example, the C and O comprising functionalities can comprise C(O)OH, C(O), or (OH) groups.

The invention includes a method of forming the photocatalytic nanocomposite comprising dispersing carbon nanotubes which are then chemically oxidized to produce functional groups on the surface of the nanotubes. The surface functionalized nanotubes are then processed with a metal oxide photocatalyst sol-gel precursor to form a continuous nanoscale metal oxide photocatalyst layer which is covalently or ionically bound to the nanotube surface. The photocatalyst nanocomposite is then preferably heated to a temperature between 350° C. to 550° C. to form the anatase structure of $TiO_2$.

The invention also includes a method of destroying biological agents by irradiating the photocatalyst nanocomposite with light having photon energies which equal or exceed the bandgap energy of the photocatalyst nanocomposite and exposing a fluid contaminated with a biological agent to photocatalyst nanocomposites according to the invention. Since the photocatalyst nanocomposite has been discovered to be imparted significant photocatalytic activity using light in the visible spectrum, irradiation in either the visible range or the ultraviolet range or a broad spectrum provides effective destruction of biological agents. Furthermore, the photocatalyst nanocomposite maintains its activity in the dark for long periods of time after irradiation for short periods of time. This feature permits the method to be practiced using intermittent irradiation, so that periods of darkness are interspersed with periods of irradiation. The cycle of dark and irradiation does not have to be periodic.

The invention also includes a system where the photocatalyst nanocomposite is disposed on the surface of a support which can be irradiated to destroy biological contaminates in a fluid exposed to the irradiated photocatalyst nanocomposite. The system can use ambient light from the environment (e.g. sunlight), or can use another light source including a visible light source. A device such as a fan or a pump can also be incorporated into the system to direct the fluid into contact with the photocatalytic nanocomposite.

BRIEF DESCRIPTION OF THE DRAWINGS

A fuller understanding of the present invention and the features and benefits thereof will be accomplished upon review of the following detailed description together with the accompanying drawings, in which:

FIG. 1(a)-(c) show scanned high-resolution transmission electron microscopy (HRTEM) images of $TiO_2$ coated multi-walled nanotubes (MWNTs) according to the invention, while FIG. 1(d) shows the $TiO_2$ coating fragment after burnout of the MWNT core.

DETAILED DESCRIPTION

Figure 1:
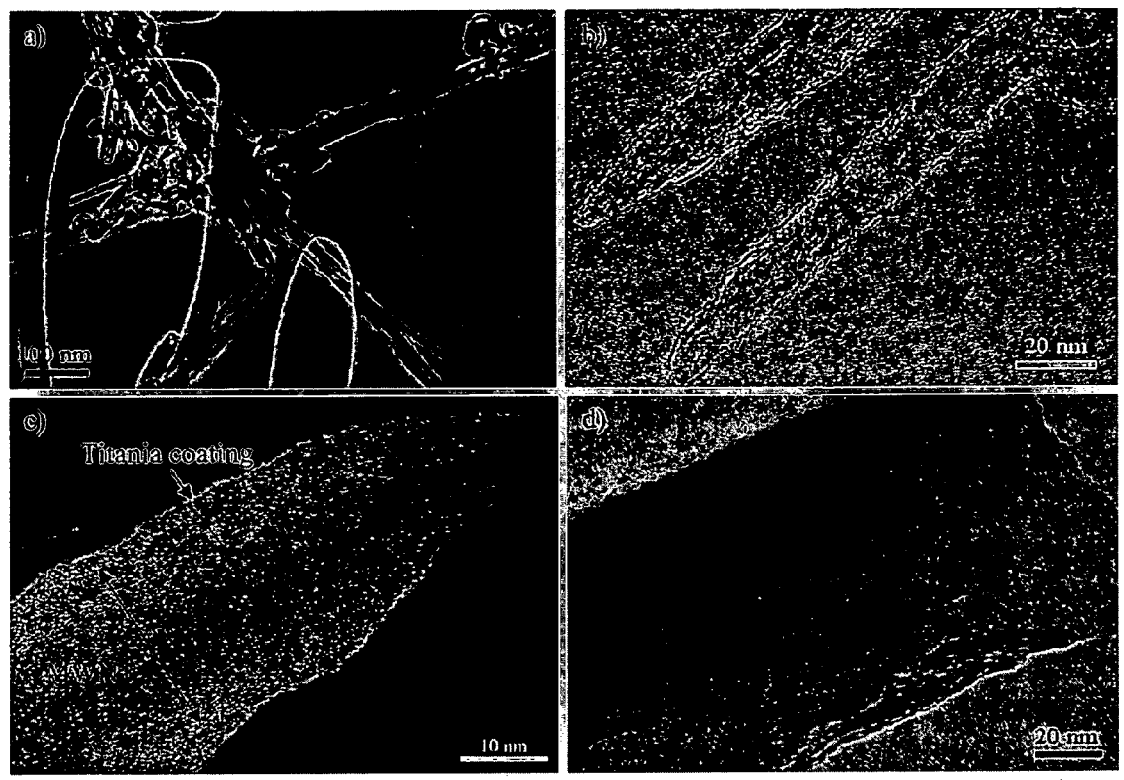

A photocatalyst nanocomposite comprises a carbon nanotube core, and a nanoscale photocatalyst coating layer covalently or ionically bound to the nanotube core. The coating is disposed on the outside of the nanotube. Previous photocatalyst nanotubes have not involved the chemical bonding of the metal oxide photocatalyst to the carbon nanotubes.

In a preferred embodiment, the photocatalyst coating is a continuous coating. Continuous surface coverage shields the carbon nanotube from direct contact with the environment. Therefore, only the photocatalytically active species, such as $TiO_2$, is exposed and the carbon nanotube is used for charge scavenging and storage. The efficacy of photocatalyst coated nanotubes according to the invention as a biocide have been shown to be superior to $TiO_2$ alone by around a factor of 200 for a given mass of $TiO_2$. This can be seen in Table 1 described below where the same mass of $TiO_2$ has half of the activity of the $TiO_2$ coated nanotubes according to the invention even though the $TiO_2$ accounts for only about 0.5% of the mass of the nanocomposite.

The nanotubes can be single wall nanotubes (SWNTs) or multi-wall nanotubes (MWNTs). It is preferred that the nanotubes be metallic nanotubes. In a preferred embodiment, MWNTs, which are generally metallic, are used.

Although described in terms of a photocatalyst layer disposed on nanotube cores, it is possible that other electrically conductive materials can be used together with the nanotubes, or as alternatives to nanotubes. For example, it may be possible for electrically conductive carbon black to replace nanotubes as carbon black provides an electronic band structure similar to the band structure provided by carbon nanotubes. Accordingly, metallic carbon black of nanoscale dimensions can provide similar charge scavenging and storage properties for the nanocomposite. Carbon black has the advantage that it is generally obtainable at a fraction of cost of carbon nanotubes.

The coating layer has a nanoscale thickness, preferably being 1 to 10 nm, and most preferably from 1-5 nm. The advantage of a thin photocatalyst layer is an increase in photocatalytic efficiency. The photocatalytic efficiency is inversely related to the photocatalyst thickness. This is caused by an increasing probability for recombination of the formed electron-hole pair before the hole has migrated to the surface of the photocatalyst as the photocatalyst layer thickness increases. Although described herein generally using the photocatalyst $TiO_2$, the photocatalyst can comprise a variety of semiconductors, such as, but not limited to ZnO and $Fe_3O_4$.

Photocatalyst nanocomposites according to the invention can be formed in the following exemplary non-limiting way. MWNTs can be obtained commercially (Alfa Aesar, 3-24 nm outer diameter, 0.5-5 μm). Such commercial nanotubes do not have functional groups on the nanotube surface. The MWNT surfaces can then be chemically treated using a chemical oxidation process to produce surface functionalization, such as using a nitric acid process at a temperature between 120 and 160° C. Other reagents can be used for the oxidation such as sulfuric acid. The functionalized surface is modified so that thin layers of metal oxides can be ionically or covalently attached thereto. Following chemical oxidation, the nanotubes become partially covered with acidic functional groups, C(O)OH, and cabonyl, C(O), and hydroxy, (OH) functional groups.

These groups are used for initiating chemical reactions and adsorption of ions from solution. Sol-gel processing is preferably used for this purpose. For example, a titanium(III) sulfate (99.9+%) solution can be stirred with functionalized MWNTs dispersed $H_2O$ for 30 minutes to 3 hours. The resulting $TiO_2$ coated MWNTs can be centrifuged, and dried. The dried $TiO_2$ coated MWNTs are preferably then heated to a temperature sufficient to result in crystallization of the $TiO_2$, such as at 500° C. for at least one hour in air. Transmission electron microscopy has shown that the $TiO_2$ coating is continuous over the entire nanotube outer surface. The bonding of the $TiO_2$ to the MWNT provided by the above method provides enhanced photocatalytic efficiency and modification of the properties of the $TiO_2$ displayed by the invention. Unexpectedly, the bonding of the $TiO_2$ to the MWNT, ($TiO_2$-MWNT), provides significant photocatalytic activity when irradiated with visible light (400 nm to 750 nm) in addition to the conventionally used ultraviolet light. This is surprising because it is well known in the art that $TiO_2$ is a semiconducting photocatalyst having a room temperature band gap energy of about 3.2 eV. Thus, for room temperature operation, photocatalyst systems prior to the invention using $TiO_2$ required irradiation with photons having wavelengths less than about 385 nm (UV) to display significant photocatalytic activity.

Although not needed to practice the claimed invention, Applicants, not seeking to be bound to theory, present a mechanism which explains the superior photocatalytic performance demonstrated by nanocomposites according to the invention. The carbon nanotube electronically coupled to the photocatalyst is believed to provide a sink for photogenerated electrons generated by the photocatalyst upon irradiation thus allowing photogenerated holes to enjoy significantly longer lifetimes as compared to when nanotubes are absent. For example, the retardation of the recombination provided by the invention can significantly enhance the biocidal photocatalytic activity provided and permit some efficacy in the dark after the irradiation is turned off.

Photocatalytic composites according to the invention, such as $TiO_2$-MWNT, are expected to be useful for a variety of existing photocatalytic processes. In an application having emerging importance, photocatalytic composites according to the invention are expected to be highly useful for the rapid deactivation of biological agent such as spores. Such materials are expected to become a significant tool for cleaning up of contaminated sites and to counter-bioterrorism.

Figure 8:
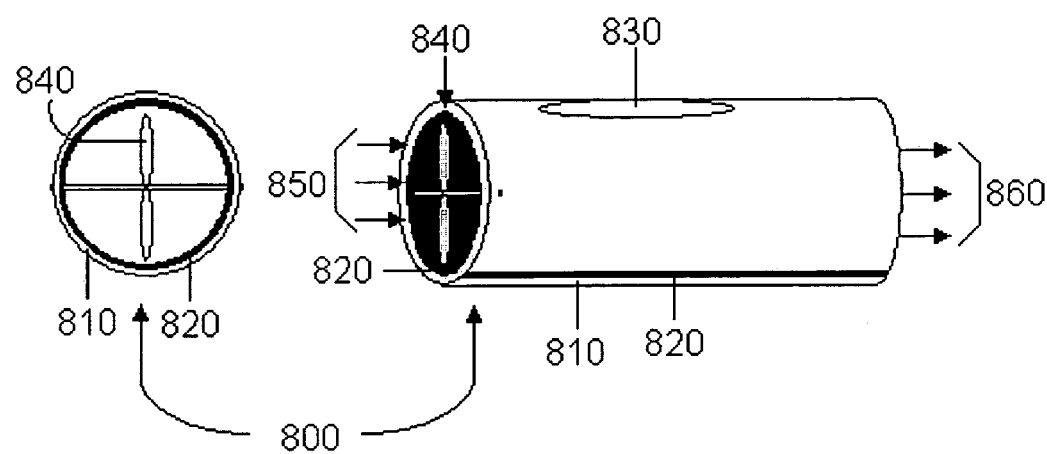
FIG. 8 shows a cylindrical tube embodiment of a system for decontaminating a fluid where the photocatalytic nanocomposite is supported by the inside wall of the tube and is irradiated by external ambient light through an optically transparent window.

The invention can be embodied as a system for the decontamination of fluids. These systems include photocatalytic nanotubes supported on a substrate surface over which the fluid, either gaseous, i.e. air, or liquid, i.e. water, is contacted. Photons of sufficient energy to match or exceed the band gap of the photocatalyst as modified by the nanotube bound thereto can be directed from a source that is either natural, i.e. sunlight, or artificial, i.e. lamps, which include visible and/or ultraviolet light. FIG. 8 gives a schematic of a system 800 for decontamination of air through a cylindrical tube showing both a side view and an end view. The system 800 includes a support, which is shown as the surface of cylindrical tube 810, but can also be a flat surface, irregularly shaped surface, fibers, tube bundles, or any other surface that provides mechanical support. The photocatalytic nanocomposite 820 is disposed onto the tube 810, such as from a suspension of the photocatalytic nanocomposite in a liquid. An adhesive, such as a silane coupling agent, can be used if needed depending upon the chemical nature of the of the surface of the support. A source of photons of that provide photons having energies that meet or exceed the band gap energy of the photocatalytic nanocomposite is provided. As noted above, the required photon energy is less than the minimum photon energy known in the art to be required by the photocatalyst (3.2 eV). This source is displayed as a single window 830 through which ambient light enters the cylindrical tube. The ambient light can be sunlight or from a lamp.

As illustrated in FIG. 8 with a 2 blade fan 840 is used to promote the flow of the fluid for disinfection into the entrance 850 of system 800 onto the surface of the photocatalytic nanocomposite at a rate faster than unaided diffusion to the exit 860 of system 800. Pumps (not shown) can also be incorporated for use with gases or liquids or any mode of generating a pressure differential can be employed.

Alternatively, to achieve irradiation of the photocatalytic nanocomposite a lamp could be placed within the system 800, multiple windows may be used, mirrors or optical fibers may be incorporated to direct the light, a transparent support may be used.

EXAMPLES

The present invention is further illustrated by the following specific Examples, which should not be construed as limiting the scope or content of the invention in any way.

Example 1

Synthesis and Characterization of $TiO_2$-MWNT Nanocomposites: Commercially available arc-discharged MWNTs (Alfa Aesar, 3-24 nm outer diameter, 0.5-5 μm) were used as templates and the functionalization of the carbon surfaces was performed by chemical oxidation according to a method disclosed by Tsang et al., Nature, vol. 372, pp. 159-162, 1994. Oxidation was performed by dispersing 300 mg of MWNTs in 200 mL of 70% $HNO_3$ by sonification for 30 minutes followed by refluxed with magnetic stirring at 140° C. for 10 hours. In this manner the MWNT surface was modified so that a thin layers of metal oxides could be attached via sol-gel processing. Although not used in this Example, uniformity of the suspension of the nanotubes in the solution can be aided by stabilizing agents, such as surfactants (e.g. sodium dodecyl sulfate (SDS)) and certain polymers.

The nanotubes obtained had an outer diameter less than 20 nm and their surfaces were partially covered with acidic functional groups. After the oxidation process the MWNT samples were characterized by HRTEM (JEOL 2010F). The walls were damaged and the tips were almost always opened. It was concluded that these opened tubes contained a considerable number of functional groups (C(O)OH, C(O), OH), as indicated by acid base titration and IR spectroscopy. Subsequently, 20 μL of Titanium(III) sulfate (99.9+%) solution was stirred with the surface oxidized MWNTs dispersed in 10 mL of $H_2O$ for 1 hour and washed with $H_2O$ repeatedly. The resulting $TiO_2$ coated MWNTs were centrifuged, dried at 60° C. for two days, and then heat treated at 500° C. for six hours in air for crystallization of the $TiO_2$.

After each step of the sol-gel process, samples were collected and the nanostructure was characterized with HRTEM confirming the chemical elements using energy dispersive x-ray spectroscopy (EDS). The heat treatment was performed with thermogravimetric analysis/differential thermal analysis (TGA/DTA, Netzsch STA 449C) monitoring changes in mass and energy of the samples. Both titania coated MWNTs and impurities ($TiO_2$ nanoparticles and/or $TiO_2$ coated carbon nanoparticles) were observed. The size of the impurities ranges from several nanometers to tens of nanometers. Since the impurities were considerably smaller than the $TiO_2$-MWNT nanocomposite, they were separated by sonification followed by microfiltration, a known process used in non-destructive carbon nanotube purification.

Figure 2:
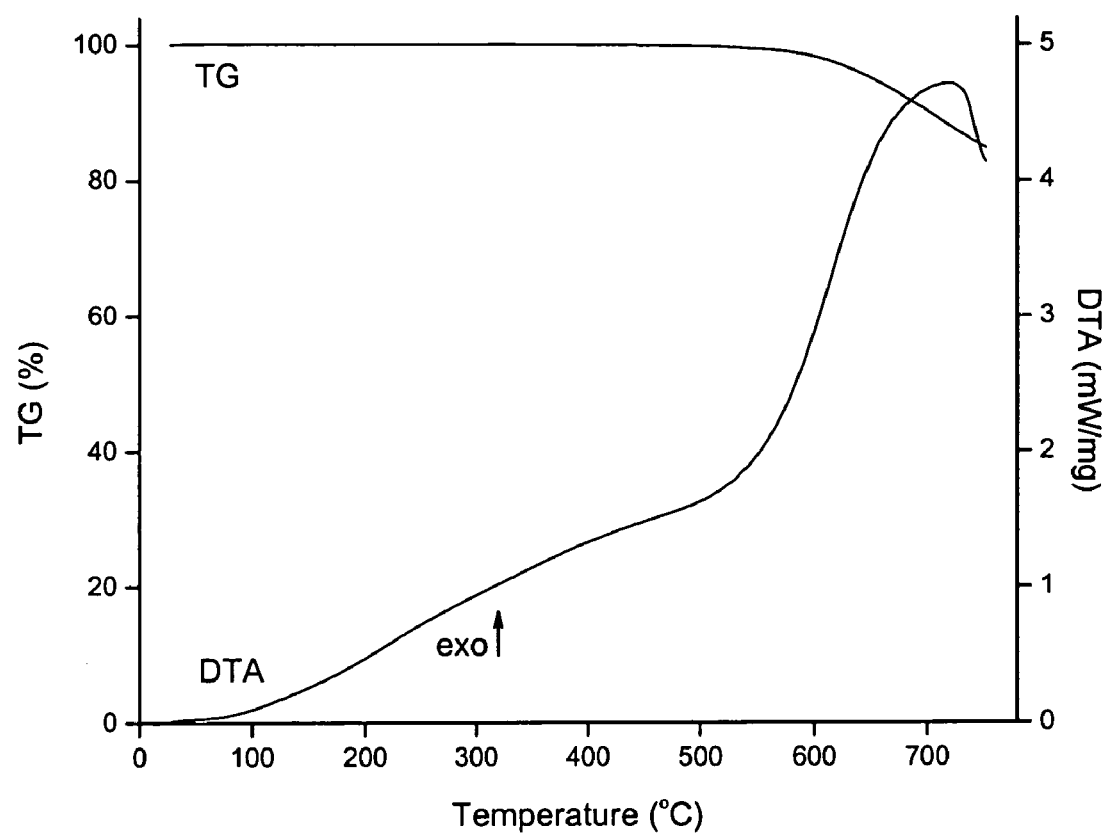
FIG. 2 shows a thermogravimetric analysis (TGA) and thermal differential analysis (DTA) of dried $TiO_2$ coated MWNTs in air.

FIGS. 1(a)-(c) show HRTEM images of $TiO_2$ coated MWNTs according to the invention, while FIG. 1(d) shows a $TiO_2$ coating fragment after burnout of the MWNT core. The sol-gel reaction the samples were dried, and then heat treated to 500° C. for crystallization of the $TiO_2$ coating. Thermogravimetric characterization and differential thermal analysis shown in FIG. 2 demonstrate a gradually increasing exothermic reaction, which was attributed to changes in the $TiO_2$ structure since no weight loss was observed.

Figure 3:
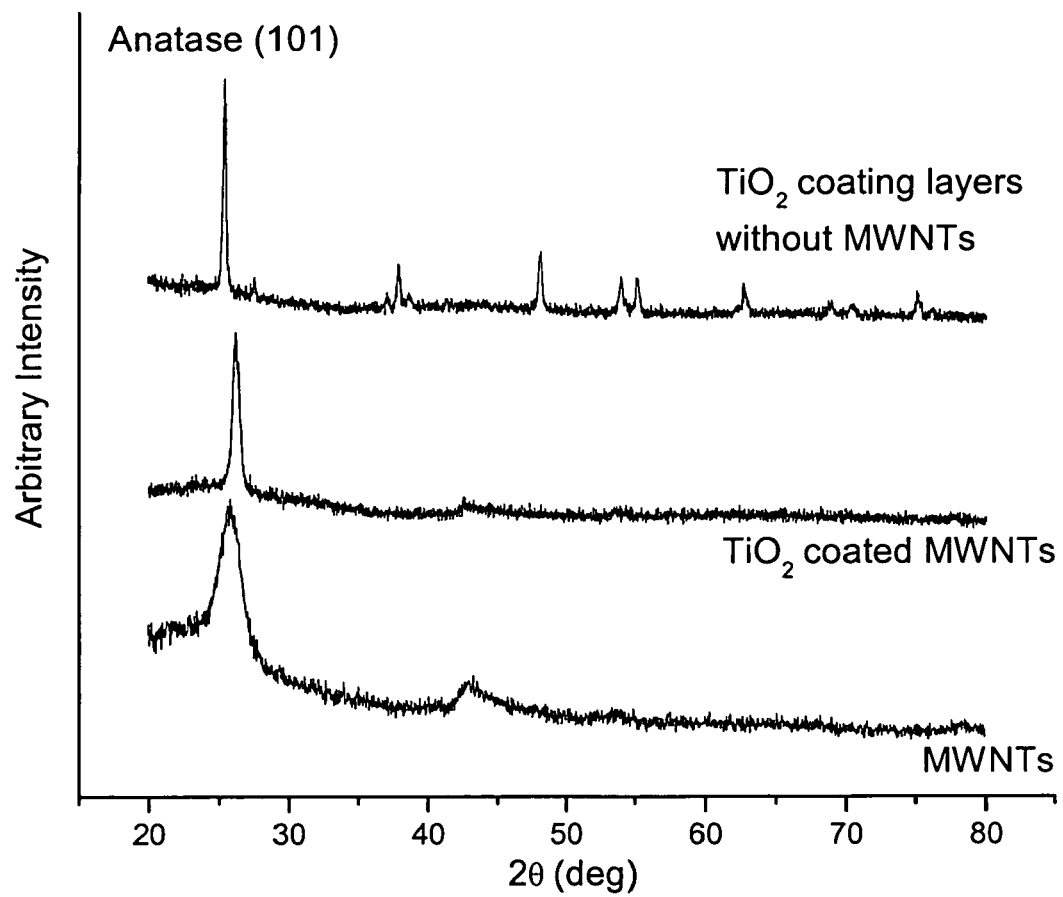
FIG. 3 are XRD patterns of raw MWNTs, a $TiO_2$-MWNT nanocomposite according to the invention, and $TiO_2$ coating layers after burnout of MWNTs at 750° C. in air.

Pure $TiO_2$ coating samples were prepared for XRD comparison studies by burning out the carbon from the $TiO_2$-MWNTs of Example 1 at 800° C. in air for three hours. $TiO_2$ coating fragments (see FIG. 1(d)) could be observed after the MWNT removal. FIG. 3 shows the XRD characterization of the untreated MWNTs and the $TiO_2$-MWNT. Despite the $TiO_2$ coating on MWNTs, no $TiO_2$ patterns could be detected for the nanocomposite. This is likely due to the very thin coating thickness (~3 nm) of the $TiO_2$ in the nanocomposite. The titania phase can be assumed to be anatase in analogy to other reports, e.g. sulfate solutions of titanium always give anatase, the metastable form of $TiO_2$. Anatase requires heat treating at 920° C. for 1 hour into rutile that is more stable with respect to anatase. Therefore, the nanocomposites produced are anatase composites as the samples were not heat treated to sufficient temperatures to form rutile. After burnout of the MWNTs at 800° C. the presence of anatase was confirmed by XRD as shown in FIG. 3.

Example 2

Spore Preparation and Biocidal Test: *B. cereus* ATTC 2 was used as a surrogate of *Bacillus anthracis*. The bacteria were inoculated in 500 mL Erlenmeyer flasks containing 99 mL of Columbia broth supplemented with 1 mL of 10 mM $MnSO_4.H_2O$. Foam plugs were used to allow air access and prevent contamination. Liquid cultures were incubated for three days at 35±2° C. an orbital incubator-shaker (Model C24, New Brunswick Scientific) at 250 rev/min. Spores were harvested and purified using the lysozyme treatment. The heat shock treatment (80° C., 10 minutes) was applied following the purification process to ensure killing of vegetative cells. Spore suspensions were stored in sterile deionized water and refrigerated at 4° C. until use. Three types of spore suspensions were prepared; (i) the control sample by suspending 10 mL of spore suspension in 20 mL of sterile deionized water, (ii) the experimental sample with 3 mg of commercial $TiO_2$ nanoparticles (Degussa P25, primarily anatase with BET surface area of 50 $m^2$/g and average particle size of 21 nm) into 20 mL of sterile deionized water, sonicating (30 min) in an ice water bath, and adding a volume of 10 mL of spore suspension giving the total amount of 30 mL of spore plus $TiO_2$ suspension, and (iii) the experimental sample with 0.8 mg of $TiO_2$-MWNT nanocomposites (anatase coating with BET surface area of 172 $m^2$/g) into 20 mL of sterile deionized water, sonicating, and adding of spore suspension as (ii). Each sample was transferred to a sterile 100×15 mm sterile Petri dish with a sterile magnetic stirring bar.

Figure 4:
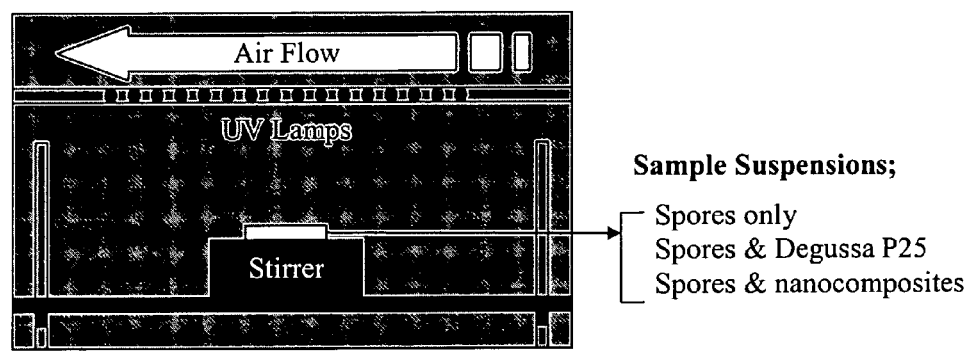
FIG. 4 shows a schematic diagram of an exemplary UV chamber for biocidal testing.

The UV chamber (shown in FIG. 4) comprising a bank of sixteen 350 nm UV lamps (RPR-3500A, Southern New England), a lamp cooling fan, and an adjustable sample holder was used throughout this Example. A magnetic stirrer was placed on the sample holder at the center of irradiation area to provide mixing of experimental suspension. The sample holder was adjusted to give a distance of 10 cm measured from the lamp surface to the initial suspension surface. The UV intensity was measured using a radiometer (Model 30526, Eppley Laboratories Inc.) and a correction coefficient specifically for solar UV was applied. The UV lamps were stabilized for 30 minutes to obtain constant intensity (92 $W/m^2$) before each test.

Samples were collected immediately after the suspension was exposed to UV and subsequently every 30 minutes. For each sampling, a volume of 0.25 mL of the suspension was collected four times, which resulted in the total volume of 1 mL into a sterile culture tube, which was wrapped with aluminum foil. The tube was capped and refrigerated immediately after sampling until use.

The sample was analyzed for survival ratio of *B. cereus* spores at any sampling time. Colony forming units (CFU) were enumerated by spreading the cultures onto tryptic soy agar plates. The cultures were serially diluted using sterile phosphate buffered saline (PBS) containing 2 mM of the ionic surfactant sodium dodecyl sulfate (SDS). The presence of surfactant in the diluting media was crucial because *B. cereus* spores tend to agglomerate in water; in following they are often found to be the most hydrophobic among *Bacillus* species. Experimental studies showed that the coefficient of variation ($C_V$) of *B. cereus* CFU was maintained below 10% when 2 mM of SDS was added to the diluting media (PBS). The plated dishes were incubated at 35° C. for 12 hours.

Sample analysis was used to generate the relationship between the survival ratio of viable spores and UV irradiated time. $LD_{90}$ values obtained from this relationship were used to characterize the system performance. Also, the decimal reduction time (D values) obtained from the linear portion of the $log_{10}$ survival ratio and UV irradiated time plots were used as another characterizing parameter. Both $LD_{90}$ and D values were obtained from triplicate experiments of each system, and the mean and standard deviation were reported.

Table 1 shown below summarizes the results for each system. Degussa P25 alone gave no UV enhancing effect on *B. cereus* spores (LD90s and D values, obtained from UV alone and from UV+Degussa P25 systems, were not significantly different at α=0.05). In contrast, the TiO2-MWNT nanocomposite according to the invention reduced the LD90 and the D value by factors of 1.8 and 2.3 respectively.

TABLE 1

Effect of commercially available $TiO_2$ particles and $TiO_2$ - MWNTs nanocomposites according to the invention under the presence of solar UV on *B. cereus* spores (Biocidal tests were repeated three times)

| System | $LD_{90}$ (min) | D value (min) |
| --- | --- | --- |
| UV | 151 ± 41 | 169 ± 40 |
| UV + Degussa P25 $TiO_2$ | 198 ± 41 | 144 ± 5 |
| UV + $TiO_2$ - MWNTs nanocomposites | 84 ± 29 | 72 ± 20 |

For all control experiments, 350 nm UV had an inactivating effect to *B. cereus* spores. However, a relatively long exposure time was required to achieve 1 log reduction of viable spores. The $LD_{90}$ value of 151 minutes and D value of 169 minutes was obtained from triplicate experiments. The plots between spore survival ratio and irradiation time (FIG. 2(a)) showed the typical shoulder followed by the exponential decay and the tail region. The tail region indicated subpopulation or agglomeration of spores, which could result in a shielding effect.

Degussa P25 has been recognized as an effective photocatalyst for killing several bacteria in previous studies and the failure of Degussa P25 to enhance the solar UV effect on *B. cereus* spores was due to the spores' high resistance. An experiment was conducted using Degussa P25 under the same protocol to investigate the effect of this commercial $TiO_2$ on *Escherichia coli* vegetative cells. The result showed that the commercial $TiO_2$, under the solar UV, completely killed *E. coli* within 1 hour (data not shown). In case of the $TiO_2$-MWNT nanocomposite, the enhanced UV effect was observed as the $LD_{90}$ and D value decreased dramatically. The biocidal efficiency must be proportional to the specific surface area of photocatalysts and the quantum yield of the photocatalytic system because the number of OH. is proportional to the specific surface area and inversely proportional to the electron-hole recombination rate.

The specific surface areas of each sample were approximately the same (3 mg of Degussa P25 with BET surface area of 50 $m^2/g$ and 0.8 mg of $TiO_2$-MWNT nanocomposite with BET surface area of 172 $m^2/g$). The electron trapping mechanism associated with the $TiO_2$-MWNT nanocomposite is assumed to be the main contribution in enhancing the biocidal photocatalytic activity mainly due to the retardation of the recombination.

Figure 5:
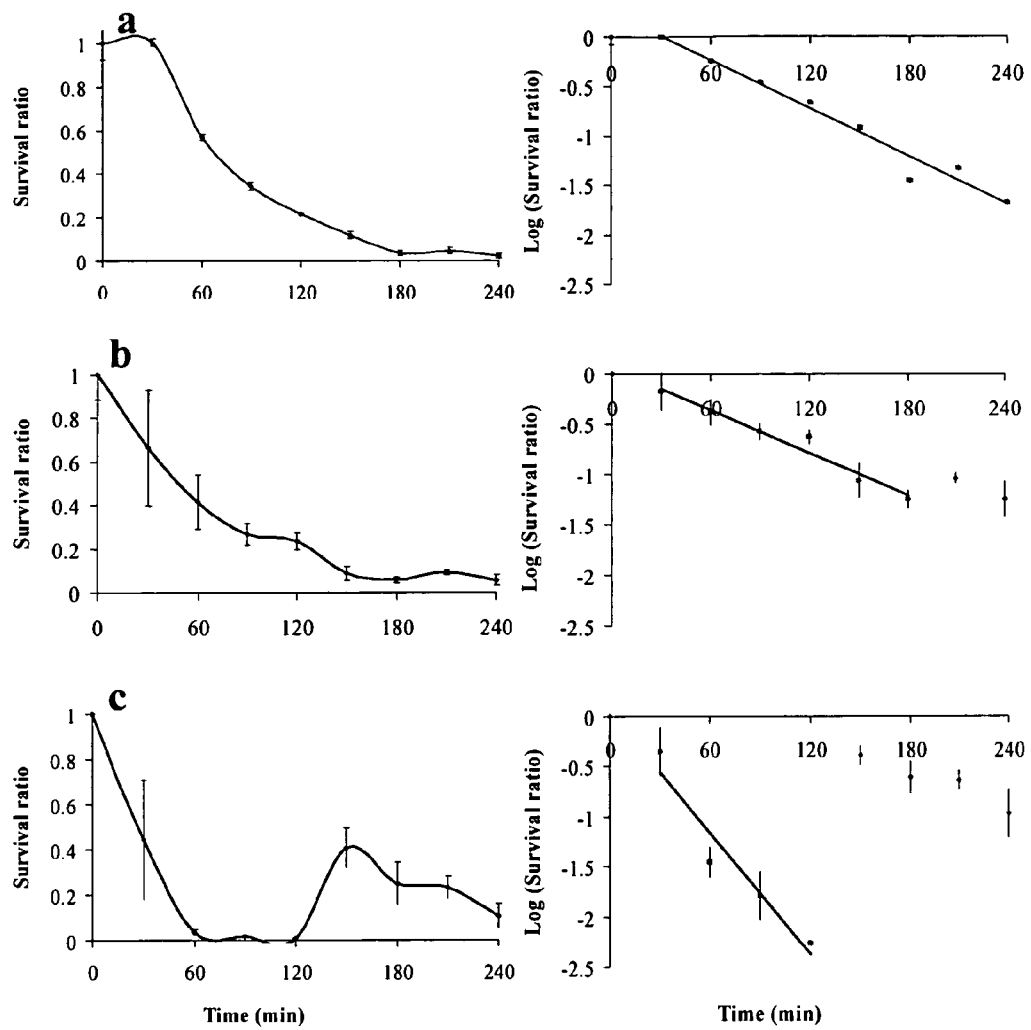
FIG. 5(a)-(c) show examples of the relationship between survival ratio of viable spores and UV irradiated time for control system (a), a system with UV and Degussa P25 $TiO_2$ (b), and a system with UV and $TiO_2$ coated carbon nanotubes according to the invention (c).

FIG. 5 shows examples of relationship between survival ratio of viable spores and UV irradiated time for a control system comprising spores suspended in deionized water (a), system with UV and Degussa P25 $TiO_2$ suspended in deionized water (b), and system with UV and $TiO_2$ coated carbon nanotubes according to the invention suspended in deionized water (c). Error bars indicate standard deviation from triplicate agar plates within the same experiment. The plots between $log_{10}$ survival ratio and irradiated time (right-hand side graphs) were fitted using the data within the exponential decay region to calculate the D values. As shown in FIG. 5(c), the invention is far more effective as compared to the system using $TiO_2$ alone.

Example 3

Figure 6:
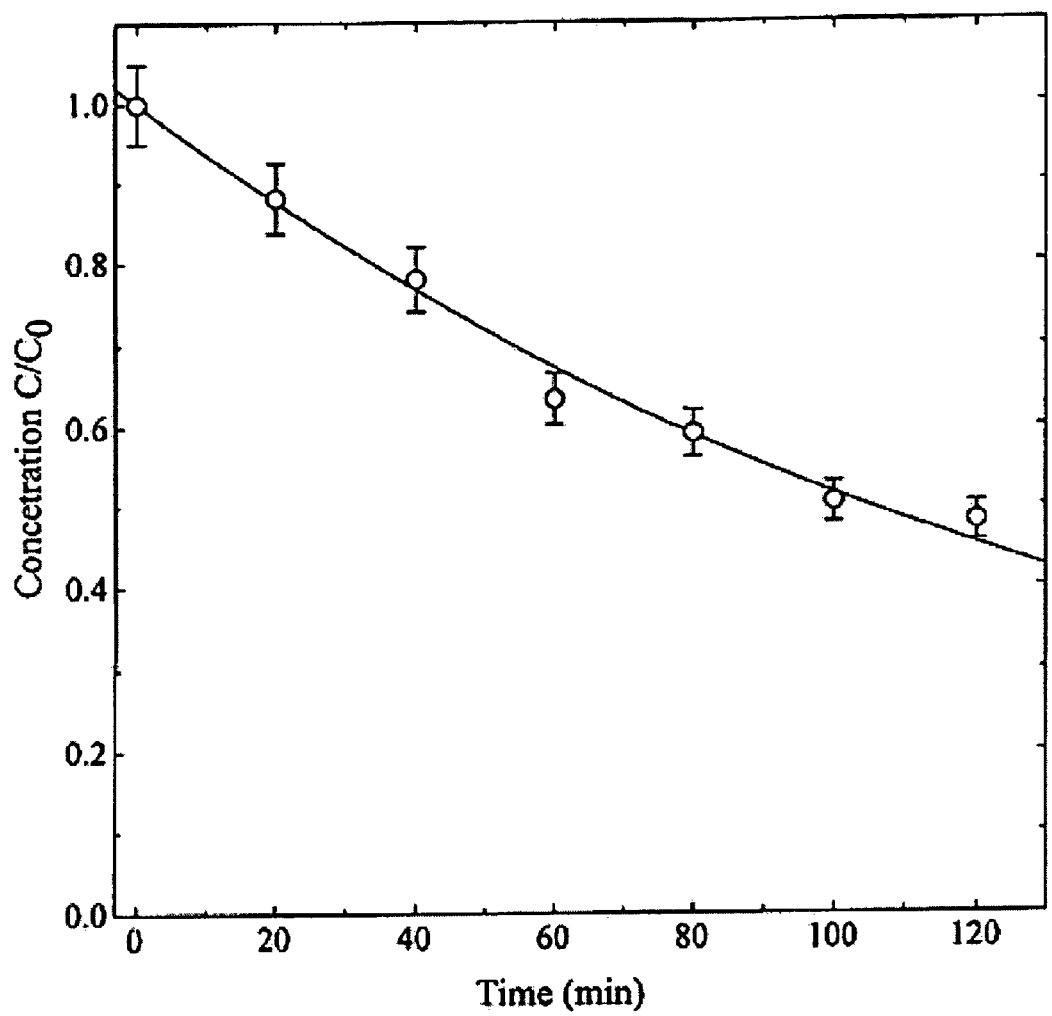
FIG. 6 shows the degradation of a dye, naphthalenedisulfonic acid, 5-((4,6-dichloro-s-triazin-2-yl)amino)-4-hydroxy-3-(phenylazo)-, disodium salt, by irradiation with visible light in the presence of $TiO_2$-MWNT nanocomposite particles according to the invention as indicated by the ratio of the dye concentration to the initial dye concentration as measured by UV-VIS spectroscopy of samples removed from the light.

Photocatalytic activity of $TiO_2$-MWNT in visible light: The photocatalytic activity of $TiO_2$-MWNT was displayed by the degradation of a dye in aqueous solution. A 3 mg sample of $TiO_2$-MWNT was dispersed in 50 mL of a 5 ppm PROCION RED MX-5B™ (naphthalenedisulfonic acid, 5-((4,6-dichloro-s-triazin-2-yl)amino)-4-hydroxy-3-(phenylazo)-, disodium salt) solution by sonification for 20 minutes. The suspension was then placed under halogen lamps of a total power of 50 $W/m^2$ which had no output of UV light. Every 20 minutes a sample was removed and the dye concentration was measured by UV-VIS spectroscopy. As can be seen in FIG. 6, the concentration of dye reduced to approximately half its initial concentration in 100 minutes. Under similar conditions with the Degussa P25 $TiO_2$ control, no measurable degradation of the dye occurred over the two hour period.

Example 4

Figure 7:
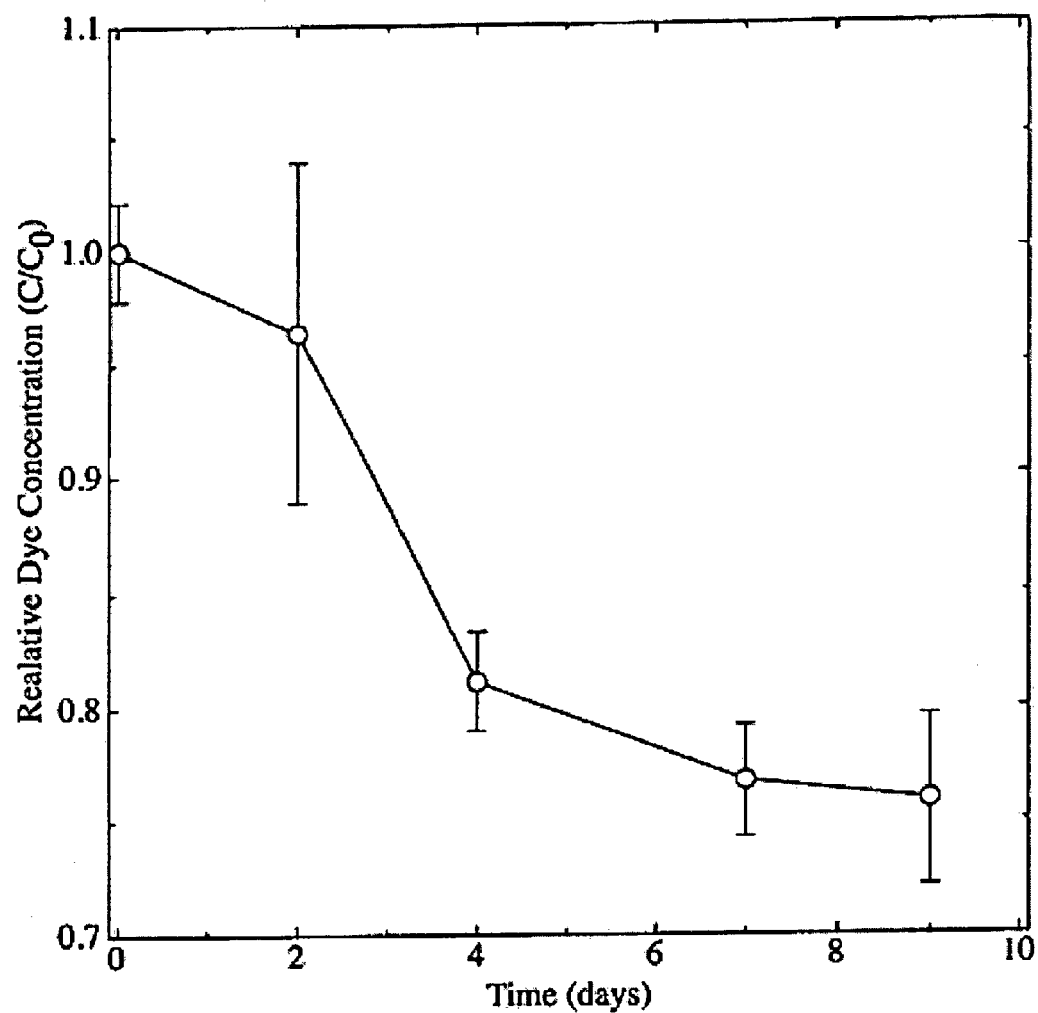
FIG. 7 shows the degradation of a dye, naphthalenedisulfonic acid, 5-((4,6-dichloro-s-triazin-2-yl)amino)-4-hydroxy-3-(phenylazo)-, disodium salt, in the presence of $TiO_2$-MWNT nanocomposite particles according to the invention by the ratio of the dye concentration to the initial dye concentration as determined by UV-VIS spectroscopy for samples of the mixture stored in the dark after irradiated at 365 nm for 10 minutes.

Photocatalytic activity of $TiO_2$-MWNT in the dark: The photocatalytic activity of $TiO_2$-MWNT according to the invention was displayed by the degradation of a dye in aqueous solution. A 1 mg sample of $TiO_2$-MWNT was dispersed in 50 mL of a 5 ppm PROCION RED MX-5B™ solution by sonification for 20 minutes. The suspension was then placed under a UV lamps of a total power of 20 $W/m^2$ for a total of 10 minutes. The suspension was then placed in a dark chamber with stirring. Every two to three days three sample were removed and the dye concentration was measured by UV-VIS spectroscopy. As can be seen in FIG. 7, the concentration of dye continued to reduce for more than a week with a reduction of the dye concentration to approximately 77% of its original concentration in a week. Under similar conditions with Degussa P25 $TiO_2$ control, no measurable degradation of the dye occurred.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

We claim:

1. A photocatalyst nanocomposite, consisting essentially of:
    a carbon nanotube core produced by an arc-discharge method, and
    a photocatalyst coating layer consisting essentially of anatase $TiO_2$ covalently or ionically bound to a surface of said nanotube core, said coating layer having a nanoscale thickness, said photocatalyst nanocomposite having a band gap energy exceeded by visible light.

2. The nanocomposite of claim 1, wherein an average of said thickness is 1 to 10 nm.

3. The nanocomposite of claim 1, wherein a band gap energy of said photocatalyst nanocomposite is less than a band gap energy of said photocatalyst.

4. The nanocomposite of claim 1, wherein said carbon nanotube provides metallic electrical conductivity.

5. The nanocomposite of claim 1, wherein said carbon nanotube is a multi-walled nanotube (MWNT).

6. The nanocomposite of claim 1, wherein said photocatalyst coating layer is a continuous layer.

7. The nanocomposite of claim 1, wherein said surface of said nanotube includes C and O comprising functionalities derived from oxidation of said surface.

8. The nanocomposite of claim 7, wherein said C and O comprising functionalities comprise at least one selected from the group consisting of C(O)OH, C(O), and (OH) groups.

9. A method of forming photocatalytic nanocomposites of claim 1, consisting essentially of the steps of:
    providing a plurality of dispersed carbon nanotubes produced by arc-discharge method;
    chemically oxidizing said nanotubes under conditions to produce surface functionalized nanotubes, said functionalized nanotubes including C and O comprising groups which form ionic or covalent bonds to metal oxides, and
    processing a metal oxide photocatalyst sol-gel precursor in the presence of said nanotubes, wherein a nanoscale anatase $TiO_2$ photocatalyst layer becomes covalently or ionically bound to said nanotubes to form the photocatalytic nanocomposite.

10. The method of claim 9, wherein said photocatalyst layer is a continuous layer.

11. The method of claim 9, further comprising the step of heating said photocatalyst nanocomposite to a temperature from 350° C. to 550° C. to form anatase.

12. The method of claim 9, wherein an average thickness of said photocatalyst layer is from 1 to 10 nm.

13. A method of destroying biological agents, comprising the steps of:
    providing a photocatalyst nanocomposite of claim 1,
    irradiating said photocatalyst nanocomposite with light whose spectrum includes photon energies which match or exceed the bandgap energy of said photocatalyst nanocomposite, and
    exposing a fluid contaminated with a biological agent to said photocatalyst nanocomposite.

14. The method of claim 13, wherein said irradiation step occurs intermittently while exposing said fluid to said nanocomposite.

15. The method of claim 14, wherein said fluid comprises air.

16. The method of claim 14, wherein said fluid comprises water.

17. A system for disinfecting fluids, consisting essentially of:
- a support;
- a photocatalyst nanocomposite disposed on said support, said photocatalyst nanocomposite comprising a carbon nanotube core produced by an arc-discharge method and a photocatalyst coating layer consisting essentially of anatase $TiO_2$ covalently or ionically bound to a surface of said nanotube core, said coating layer having a nanoscale thickness, said photocatalyst nanocomposite having a band gap energy exceeded by visible light and
- a source of photons providing photons having sufficient energy to equal or exceed a band gap energy of said photocatalyst nanocomposite, said source of photons providing visible light.

18. The system of claim 17, wherein said photocatalyst coating layer is a continuous layer.

19. The system of claim 18, wherein said source of photons comprises sunlight.

20. The system of claim 17, wherein said system is disposed inside ductwork.

* * * * *

UNITED STATES PATENT AND TRADEMARK OFFICE
CERTIFICATE OF CORRECTION

PATENT NO. : 7,541,509 B2  
APPLICATION NO. : 11/216303  
DATED : June 2, 2009  
INVENTOR(S) : Wolfgang M. Sigmund et al.

Page 1 of 1

It is certified that error appears in the above-identified patent and that said Letters Patent is hereby corrected as shown below:

<u>Column 1,</u>

Line 48, "(OH.) generated" should read --(OH˙) generated--.

<u>Column 9,</u>

Line 4, "OH. is" should read --OH˙ is--.  
Lines 54-55, "placed under a UV lamps" should read --placed under a UV lamp--.  
Lines 57-58, "three sample were removed" should read --three samples were removed--.

Signed and Sealed this

Eighth Day of September, 2009

David J. Kappos  
*Director of the United States Patent and Trademark Office*